United States Patent
Rosenbloom

(10) Patent No.: US 7,175,987 B2
(45) Date of Patent: *Feb. 13, 2007

(54) COMPOSITIONS AND METHODS FOR TREATMENT OF HERPES

(75) Inventor: Richard A. Rosenbloom, North Wales, PA (US)

(73) Assignee: The Quigley Corporation, Doylestown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/371,974

(22) Filed: Mar. 9, 2006

(65) Prior Publication Data

US 2006/0147989 A1    Jul. 6, 2006

Related U.S. Application Data

(63) Continuation-in-part of application No. 11/012,764, filed on Dec. 14, 2004, which is a continuation-in-part of application No. 10/359,889, filed on Feb. 6, 2003, which is a continuation-in-part of application No. PCT/US02/24794, filed on Aug. 6, 2002.

(51) Int. Cl.
*C12Q 1/68*   (2006.01)

(52) U.S. Cl. ............................. 435/6; 435/5

(58) Field of Classification Search ............ 435/5, 435/6

See application file for complete search history.

(56) References Cited

U.S. PATENT DOCUMENTS

| 5,908,857 | A | 6/1999 | Suzuki |
| 6,030,980 | A | 2/2000 | Suzuki |
| 6,063,381 | A | 5/2000 | Staggs |
| 6,274,177 | B1 | 8/2001 | Wu et al. |
| 6,291,533 | B1 | 9/2001 | Fleischner |
| 6,391,346 | B1 | 5/2002 | Newmark et al. |
| 6,841,544 | B2 | 1/2005 | Gelber et al. |

FOREIGN PATENT DOCUMENTS

JP    03228667    10/1991

*Primary Examiner*—Ali R. Salimi
(74) *Attorney, Agent, or Firm*—Knoble Yoshida & Dunleavy, LLC

(57) ABSTRACT

Prophylactic and treatment methods for treatment of herpes, as well as methods for reducing or preventing the transmission of herpes. The methods comprise the step of administering to a mammal, an amount of a composition having a first ingredient obtainable from ginger; a second ingredient obtainable from green tea; an optional third ingredient obtainable from turmeric; an optional fourth ingredient obtainable from horseradish, and an acceptable carrier. When administered the composition is effective to reduce the incidence of contracting herpes, to reduce or prevent transmission of herpes, to reduce the herpes virus, or to alleviate one or more symptoms of herpes. Also disclosed are suitable formulations for delivery of the compositions for use in the methods of the invention.

33 Claims, No Drawings

COMPOSITIONS AND METHODS FOR TREATMENT OF HERPES

This application is a continuation-in-part of U.S. patent application Ser. No. 11/012,764, filed on Dec. 14, 2004, currently pending, which, in turn, is a continuation-in-part of U.S. patent application Ser. No. 10/359,889 filed on Feb. 6, 2003, currently pending; which, in turn, is a continuation-in-part of International Patent Application No. PCT/US02/24794, filed on Aug. 6, 2002, designating the United States of America and published in English, now abandoned.

BACKGROUND OF THE INVENTION

1. Field of the Invention

The present invention relates to methods for treating, reducing or preventing one or more symptoms or adverse effects of a herpes infection and to methods for reducing the infectivity or transmission of herpes infections.

2. Description of the Related Technology

Viral pathogenesis is the method by which viruses produce disease in the host. The pathogenesis of viruses centers on the mechanisms of viral injury to discrete populations of cells in particular organs to produce signs and symptoms of disease in a particular host.

To initiate an infection the virus must gain entry to the host cell. Entry routes are dependent on the virus and include the skin, eyes, respiratory, GI and urogenital tracts as well as the circulatory system. Some viruses localize their tissue injury in close proximity to their site of entry, particularly the viruses that infect the upper respiratory tract such as influenza, parainfluenza, rhinoviruses and coronavirus. Once the viral particle has invaded the cell, viral coded proteins direct the cell to replicate the viral genome and produce viral specific proteins. These proteins are assembled into complete virions along with the viral genome and released. In the case of enveloped viruses, the virions acquire a lipid membrane and will insert through this lipid membrane, viral specific glycoproteins. The enveloped virus families include the Herpesviridae, Retroviridae, Orthomyxoviridae, Paramyxoviridae, Flaviviridae, Togaviridae and Coronaviridae. The rhinoviruses are members of the Picornaviridae, which are not enveloped.

Viruses have evolved a number of mechanisms to enter a host cell and initiate infection. To fuse to the cell membrane, viruses have a membrane glycoprotein with membrane fusion activity. Many enveloped virus induce a receptor-mediated endocytosis after binding to the cell surface receptor, causing the cell to form an endosomal vesicle. Once inside the vesicle, the virus particle undergoes the uncoating process. This insures that the optimal pH for the viral genome is maintained and that the viral genome is protected from cellular nucleases.

Ocular herpes is a recurrent viral infection that is caused by the herpes simplex virus and is the most common infectious cause of corneal blindness. There are two types of herpes simplex viruses. HSV-1 primarily infects the mouth, face and eyes. HSV-2 primarily causes genital infections. However, either HSV-1 or HSV-2 can manifest itself as an ocular disease.

Ocular herpes can produce painful sores on the eyelids or surface of the eye and may cause inflammation of the cornea. Prompt treatment with anti-viral drugs helps to stop the herpes virus from multiplying and destroying epithelial cells. However, the infection may spread deeper into the cornea and develop into a more severe infection called stromal keratitis, which causes the immune system to attack and destroy stromal cells.

Like other herpes infections, ocular herpes can be controlled but not cured. An estimated 400,000 Americans have had some form of ocular herpes. Topical antiviral treatment of ocular herpes is available, but the most frequently used topical agent can be toxic to the corneal epithelium. Thus, there is a need for a safe, topical virucidal agent that can eliminate the virus in initial or recurring episodes and than can inhibit ocular herpes outbreaks due to contact lenses, drugs and cosmetics coming into contact with the cornea.

Genital herpes is an infection of the genitals, buttocks or anal area caused by the herpes simplex virus (HSV). HSV-2 is most commonly associated with genital herpes, though HSV-1 may cause up to about 10% of cases of genital herpes. HSV-2 can also infect the mouth. According to the Centers for Disease Control and Prevention, 1 out of 5 American teenagers and adults are infected with HSV-2. Medicines available to treat genital herpes include acyclovir, famciclovir and valacyclovir. However, there remains a need for alternative medicines for treatment of genital herpes.

Therefore, there exists a need in the field to provide a prophylactic method for the reduction of the incidence of contracting an illness caused by a microbial organism.

SUMMARY OF THE INVENTION

In a first aspect, the present invention relates to a method for the use of an anti-microbial composition to treat herpes. The method comprises the steps of administering to a mammal that has been, or will be, exposed to herpes, an amount of an anti-microbial composition having a first ingredient obtainable from ginger; a second ingredient obtainable from green tea; and an acceptable carrier. The amount of anti-microbial composition is effective, when administered in a manner whereby the anti-microbial composition comes into direct contact with the herpes virus, for treating, reducing or preventing one or more symptoms or adverse effects of a herpes infection and for reducing the infectivity or transmissivity of herpes infections.

These and various other advantages and features of novelty that characterize the invention are pointed out with particularity in the claims annexed hereto and forming a part hereof. However, for a better understanding of the invention, its advantages, and the objects obtained by its use, reference should be made to the accompanying descriptive matter, in which there is described a preferred embodiment of the invention.

DETAILED DESCRIPTION OF THE PREFERRED EMBODIMENTS

In a first aspect, the present invention relates to a method for the treatment of herpes by administration of a composition which includes ingredients that can be obtained from ginger, green tea and, optionally, turmeric in a manner whereby the composition comes into direct contact with the herpes virus in the body.

As used herein the term "flavors" includes both fruit and botanical flavors.

As used herein the term "sweeteners" includes sugars, for example, glucose, sucrose and fructose. Sugars also include high fructose corn syrup solids, invert sugar, sugar alcohols including sorbitol, and mixtures thereof. Artificial sweeteners are also included within the scope of the term, "sweetener."

As used herein, the term "acceptable" means a component that is suitable for use with humans and/or animals without undue adverse side effects (such as toxicity, irritation, and allergic responses), commensurate with a reasonable risk/benefit ratio.

Further, as used herein, the term "safe and effective amount" refers to the quantity of a component, which is sufficient to yield a desired therapeutic response without undue adverse side effects (such as toxicity, irritation, or allergic responses), commensurate with a reasonable risk/benefit ratio when used in the manner described herein.

The term "inhibiting" a microbe, as used herein, refers to reducing or preventing further growth of the microbe, or preventing the microbe from attaching to normal cells, and/or the elimination of some or all of the infectious particles from the human or animal being treated. Suitable methods for determining microbe inhibition are discussed in the examples.

The term "transmissivity" as used herein refers to the transfer of a microbe from one host to another.

All active compounds used in the present invention may be obtained from other sources, if available. Thus, the phrase "which can be obtained from" or the phrase "which may be obtained from" is meant to encompass compounds or compositions that are obtainable from turmeric, ginger, or green tea, and therefore encompasses synthetic forms of the same compounds and/or compositions as well as the same compounds and/or compositions obtained from other sources.

In a first embodiment, the composition used in the method of the present invention includes a first ingredient obtainable from ginger, and a second ingredient obtainable from green tea, in a safe and effective amount to provide one or more of the beneficial effects in the treatment of herpes described herein.

The first ingredient of the composition of the present invention may be obtained from ginger (*Zingiber officinale*, also commonly called ginger root). Native to southern Asia, ginger is a 2- to 4-foot perennial that produces grass-like leaves up to a foot long and almost an inch wide. Ginger root, as it is called in the grocery store, actually consists of the underground stem of the plant, with its bark-like outer covering scraped off.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The first ingredient of the composition of the present invention, which may be obtained from ginger, can be incorporated in the composition of the present invention in many different forms including extracts such as ginger powder extracts, ginger fluid extracts, ginger powder including ginger root powder, and one or more active compounds of ginger, parts of, or whole ginger plants, tinctures thereof, and mixtures thereof. Preferably, the first ingredient of the composition of the present invention is selected from ginger extract, and ginger root powder.

Each gram of the composition of the present invention preferably contains about 1 mg to about 150 mg of ginger root powder. Most preferably, each gram of the composition contains about 6 mg to about 110 mg of ginger root powder. These ranges use, as a baseline, the use of Ginger Root Powder, ex. Stryka Botanics in the ingested formulation and Ginger Extract K (Aquaresin® Ginger), ex. Kalsec®, Inc. of Kalamazoo, Mich. in the spray formulation.

The amounts of various ingredients are given herein in terms of one form of the ingredient, i.e. ginger root powder. If that ingredient is present in another form, then the amount to be employed is that amount which will provide the same amount of the one or more active compounds as the amount of that ingredient given herein. For example, if a tincture of ginger is employed, the amount of the tincture employed will be the amount that provides the same amounts of one or more active compounds as would be provided by the amounts of ginger root powder specified above. This applies to all ingredients for which the amounts are given herein for one particular form of that ingredient.

The second ingredient of the composition of the present invention may be obtained from green tea. The second ingredient obtained from green tea may have an antioxidant effect. Green tea is the dried leaves and leaf buds of the shrub *Camellia sinensis*. It is mainly produced in China and Japan. Dried tea leaves are composed mainly of phytochemicals known as polyphenols (about 36%), principally flavonols (including catechins), flavonoids, and flavondiols. The leaves also contain plant alkaloids (about 4%), including caffeine, theobromine and theophylline.

The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The second ingredient which may be obtained from green tea, can be included in the composition in the form of green tea powder, green tea extracts such as green tea powder extracts, green tea fluid extracts, and one or more active compounds of green tea, part of, or whole green tea plants, green tea leaves, tinctures thereof, or mixtures thereof. Preferably, the second ingredient of the composition of the present invention is selected from green tea leaves, green tea powder and green tea extract. More preferably, the second ingredient of the composition of the present invention is green tea extract.

Each gram of the composition preferably contains about 1 mg to about 20 mg of green tea extract. Most preferably, each gram of the composition contains about 4 mg to about 15 mg of green tea extract. These ranges use, as a baseline, the use of Green Tea, ex. Stryker Botanics in the ingested formulation and Green Tea Extract, ex. Phytoway, Inc., ChanSha, P. R. China, in the spray formulation.

The ingredients of the composition of the present invention, which may be obtained from ginger and green tea, and turmeric, may be used in the forms of turmeric powder, ginger powder and green tea powder, each of which may be ground from the rhizome of turmeric, ginger root and green tea leaves, respectively. For a particular active compound of ginger, green tea or turmeric, for which a synthetic route is known, the active compound may be synthesized. The plant extracts, if desired, may be prepared as described below. Alternatively, turmeric powder, ginger powder, green tea powder and/or one or more of the active compounds contained therein may be purchased from commercial sources such as the Kelsec®, Inc. of Kalamazoo, Mich.

The plant extracts, e.g., turmeric extract, ginger extract, green tea extract and horseradish extract that may be used in the compositions of the invention, may be produced using common extraction procedures. Alternatively, the extracts may be purchased from commercial sources such as the Kelsec®, Inc. of Kalamazoo, Mich.

In an optional embodiment, the composition of the present invention includes one or more ingredients obtainable from turmeric, in a safe and effective amount to provide one or more of the beneficial effects described herein. Turmeric (*Curcuma longa*), or Haldi in Hindi, is used very widely as medicine as well as a common ingredient in Indian cooking. The rhizome of turmeric is used in medicine and food as a fine powder.

The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis, Chromatography and Microscopy, p. 169, Ann Arbor Science Inc., 1973). The essential oils of turmeric (*Curcuma longa*) are primarily composed of the following compounds: d-camphor (about 1%), cyclo-isoprenemyrcene (about 85%), and p-tolylmethylcarbinol (about 5%), (see E. Gunther, The Essential Oil, pp. 123–4, Van Nostrand Co., 1955).

The ingredient of the composition of the present invention, obtained from turmeric, preferably includes curcuminoids, such as curcumin (diferuloylmethane), desmethoxycurcumin (hydroxycinnamoyl feruloylmethane), and bis-desmethoxycurcumin (dihydroxydicinnamoyl methane), and mixtures of two or more of these curcuminoids.

Methods for isolating curcuminoids from turmeric are known (see Janaki and Bose, An Improved Method for the Isolation of Curcumin From Turmeric, J. Indian Chem. Soc. 44:985, 1967). Alternatively, curcuminoids for use in the present invention can be prepared by synthetic methods.

The ingredient, which can be obtained from of turmeric, can be incorporated into the composition of the present invention in a variety of different forms. Those different forms preferably include extracts of turmeric such as turmeric powder extracts, turmeric fluid extracts, one or more the curcuminoid compounds, and turmeric powder, parts of, or whole plants of turmeric, tinctures thereof, and mixtures thereof. More preferably, the optional ingredient obtainable from turmeric is a turmeric extract.

When the ingredient obtainable from turmeric is used, each gram of the composition of the present invention preferably contains about 1 mg to about 20 mg of turmeric powder extract. Most preferably, each gram of the compositions contains about 6 mg to about 15 mg of turmeric powder extract. These ranges are based on the use of Turmeric Extract 95%, ex. Pharmline, Inc. in the ingested formulation and Turmeric Root Extract (Oleoresin Turmeric), ex. Kalsec®, Inc., Kalamazoo, Mich., in the spray formulation.

Also, the composition of the present invention may include one or more ingredients obtainable from horseradish root, in a safe and effective amount to provide one or more of the beneficial effects described herein.

The optional ingredient obtainable from horseradish root may include extracts from the *Cochlearia Armoracia*. Horseradish contains volatile oils that are similar to those found in mustard. These include glucosinolates (mustard oil glycosides), gluconasturtiin, and sinigrin, which yield allyl isothiocyanate when broken down in the stomach.

Ethanol, propylene glycol and glycerin and various combinations thereof, may be optionally included in the composition of the present invention, up to about 10 percent by weight of the total as additional active ingredients. Most preferably, up to about 10 percent per total weight ethanol is added as an active ingredient. Even more preferable, 2.5 to 7 percent ethanol is added.

The processes for the preparation of pharmacologically or biologically active plant extracts in a convenient, administrable dosage form from any of the plants mentioned above, are well known in the art.

The composition of the present invention may be used to treat herpes viral infection, since the composition of the present invention has significant antimicrobial properties as demonstrated by the examples of this application. The composition of the present invention may also be used as a therapeutic composition to treat one or more symptoms of a herpes viral infection, including sore throat, congestion, laryngitis, mucositis, and/or mucous membrane inflammation by administration to a patient suffering from one or more of these symptoms or ailments.

The composition of the present invention may also be employed to reduce the transimissivity of herpes and/or as a prophylactic measure to reduce the incidence of contracting herpes. In this application of the composition of the present invention, a safe and effective amount of the composition of the present invention is administered to a mammal or that has been or will be exposed to herpes, to reduce the transmissivity of the herpes virus and/or to reduce the incidence of contracting said illness, relative to a mammal that has been or will be exposed to herpes to which the composition of the present invention has not been administered.

Preferably, the composition of the present invention may be formulated in any dosage form suitable for administration of the composition in a manner whereby it will directly contact the herpes virus in the body. Suitable dosage forms may include, but are not limited to, capsules, tablets, lozenges, troches, hard candies, powders, sprays, gels, elixirs, syrups, and suspensions or solutions.

For treatment of ocular herpes, the composition of the present invention may be formulated in conventional ocular preparations. For example, the composition may be formulated as a gel, an aqueous suspension, and an ointment. These systems may include systems that provide for in situ activation of, for example, gel formation to optimize delivery of the composition. Exemplary materials that may be suitable for inclusion in ophthalmic formulations are hydrogels, carbopols, polyacrylic acids, cellosic viscosity enhancing materials and chitosan. Important properties may include adherence to the mucin coat and the corneal surface of the eye to increase residence time of the composition.

Cyclodextrins may also be employed in ophthalmic formulations to increase the solubility of the actives in solution, for example. Hyalauronic acid may also be included to increase precorneal residence time.

Penetration enhancers may also be employed for ophthalmic treatments to help ensure direct contact between the composition and the herpes virus. Penetration may also be enhanced by formulation of the composition as colloidal systems such as liposomes, microparticles and/or nanoparticles, using conventional methods. Such systems may rely on diffusion, chemical reaction, degradation of the polymeric carrier or ion exchange to enhance penetration or delivery of the composition. Collasomes and ophthalmic lyophilisate carrier systems may also be employed to improve delivery or enhance penetration.

Collagen shields, ocular inserts, ocular films, and disposable contact lenses offer other ways to deliver the compositions of the present invention for treatment of ocular herpes. In addition, vesicular systems, and chemical delivery systems, such as prodrugs, may also be employed.

The composition of the present invention may also be formulated with an acceptable carrier. The acceptable carrier may include, but is not limited to: (a) carbohydrates including sweeteners, more preferably, fructose, sucrose, sugar, dextrose, starch, lactose, maltose, maltodextrins, corn syrup solids, honey solids, commercial tablet nutritional supplements including Emdex™, Mor-Rex™, Royal-T™, Di-Pac™, Sugar-Tab™, Sweet-Rex™, and New-Tab™; (b) sugar alcohols including mannitol, sorbitol and xylitol; and (c) various relatively insoluble excipients including dicalcium phosphate, calcium sulfate, calcium carbonate, microcrystalline cellulose and other tableting ingredients.

For genital herpes, suitable transmucosal drug delivery systems may be employed. These delivery systems are useful at least for nasal, buccal, ocular, vaginal and rectal drug delivery. Useful agents for transmucosal delivery include cyclodextrins, bile salts, surfactants, fusidic acid derivatives, microspheres, liposomes and bioadhesive agents. Also, vaginal creams, foams and jellies may be employed.

Lozenges, tablets, and troches useful for oral herpes may differ in shape, size and manufacturing technique. In the case of tablets, for oral use, the acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common acceptable carrier may further include a binder such as PEG-8000. Preferably lozenges weigh about 0.1 to about 15 grams to provide a suitable dissolution rate when taken orally. More preferably, lozenges weigh about 1 to about 6 grams.

The production of lozenges is well known in the art and anyone with ordinary skill in the art can readily produce lozenges with the compositions of the present invention. The composition is preferably stored in an airtight container and in a cool dark place. Tablets and troches can be manufactured using procedures known in the art with minor changes in the optional ingredients. Such changes are within the skill of the ordinary skilled artisan.

Alternatively, the composition of the present invention may be formulated in liquid form, such as syrups, mouthwashes or sprays, with a solvent or dispersant such as water, or other liquids and optionally in a pharmaceutically acceptable carrier, for repeated delivery of the composition to oral and oropharyngeal mucous membranes over a sustained period of time. Preferably, the treatment time is about 5 to 60 minutes, and more preferably about 20 to 30 minutes, so as to permit a prolonged contact of the composition with mouth and throat tissues. Alternatively, such formulations can be in a concentrated form suitable for dilution with water or other materials prior to use.

The composition may also be formulated in chewable forms, such as soft candy, gum drops, liquid filled candies, and chewing gum bases, or in the form of dental products, such as toothpastes and mouthwashes. In use, the chewable composition is preferably retained in the mouth over a sustained period of time of preferably about 5 to 60 minutes, and more preferably about 20 to 30 minutes. Dental products may be used in the ordinary manner of using such products.

The composition of the invention may be formulated in capsule form, with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The composition of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons, and/or conventional solubilizing or dispersion agents.

Other materials, which may optionally be included in the composition of the present invention, include resveratrol (trihydroxystilbene), inositol, other B-complex vitamins, and additional anti-inflammatories. Also, ingredients such as sweeteners, flavorants, coloring agents, dyes, preservatives, emulsifying agents, suspending agents, melting agents, excipients, demulcents and solvents or diluents such as water, ethanol, propylene glycol, glycerin and various combinations thereof, may be included in the composition of the present invention.

The optional sweeteners which may be used in the composition of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the composition.

The optional flavorants which may be used in the composition of the present invention include, but are not limited to, peppermint, peppermint-menthol, eucalyptol, wintergreen, licorice, clove, cinnamon, spearmint, cherry, lemon, orange, lime, menthol and various combinations thereof.

Preferably, the main ingredients described above, that may be derived from ginger, green tea and, optionally, turmeric, make up from about 0.5 to about 90% by weight of the total composition. More preferably, the main ingredients will make up about 10 to about 70% by weight of the total composition. Most preferably, the main ingredients make up about 20 to about 40% by weight of the total composition.

The non-carrier ingredients of the composition, including the ingredients obtainable from turmeric, ginger, and green tea as discussed above, can be increased or decreased proportionally in the composition of the present invention depending on the amount of carrier used in the composition, without substantially affecting the effectiveness of the composition for its intended use.

Reducing or preventing transmission relates to preventing or reducing the spread of herpes from one patient (infected) to another patient (non-infected). Some patients may be considered carriers of the infection. Carriers are individuals who actively shed microbes but do not suffer from an acute infection. These carriers may be said to be persistently (or chronically) infected with the microbe. In addition to the persistently infected shedder, other infective individuals may be those who are actively infected, and particularly those in the early or late stages of an acute infection. One aspect of the invention relates to administering to a mammal infected with herpes, a composition of the present invention, to prevent the spread of the disease to other mammals and/or reduce the symptoms of the disease in the infected mammal.

Prophylactic treatment is aimed at a patient that will soon be exposed to herpes or has recently been exposed to herpes. Such prophylactic treatment may be effective either alone, or to augment a vaccine. Prophylactic treatment may also be used against herpes even though there may not yet be an effective vaccine available. In the case of prophylactic treatment, the composition of the invention is administered to a patient that will be exposed to herpes or has recently been exposed to herpes for the purpose of reducing the incidence of active infection herpes in that patient. Administration is carried out in a manner whereby the composition will come into direct contact with the herpes virus in that patient, for example, in the genital area if sexual transmission of the virus is implicated.

In another aspect, the present invention relates to a method for treatment of herpes by administering to a patient infected with a herpes virus, a composition of the present invention, including ingredients that can be obtained from ginger and green tea, in a manner whereby the composition directly contacts the herpes virus. In this method, the virucidal and/or virustatic effects of the composition are employed to partially or completely eradicate the virus contacted by the composition.

In another aspect, the present invention relates to a method of reducing, treating or preventing of at least one symptom or adverse effect of herpes viral infection by administering, to a patient infected with a herpes virus, a composition of the present invention, including ingredients that can be obtained from ginger and green tea. The composition is administered in a manner whereby it will come into direct contact with the herpes virus in the body.

In the method, the patient may be a human, an in vitro cell system, or an animal. Preferably, the patient is a mammal, more preferably, a human. In the method, the virus that may be inhibited by administration of the composition of the present invention includes, among other viruses, herpes simplex viruses such as Herpes 1 Virus (HSV-1), and Herpes 2 Virus (HSV-2). The method of the present invention may be employed The symptoms, caused by a viral infection, that may be treated, reduced, or at least partially prevented by this method of the present invention, may include one or more of tingling, sores, bumps, and inflammation. Secondary symptoms of viral infection may include headache, joint pain, fever, cough, sneezing, muscle ache, running nose, dry mouth, dizziness, and other symptoms related to viral infection.

In the method, additional microorganisms that may be inhibited by administration of the composition of the present invention may also include gram-positive bacteria such as *Streptococcus, Staphylococcus*, gram-negative bacteria such as *E. coli, Pseudomonas, Haemophilus* and fungi such as *Histoplasma* and *Blastomycosis* and yeast such as *C. albicans* and *Crytococcus*.

The effective amount of the composition will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the composition, and the severity of the illness or symptom. It is within the skill of the person of ordinary skill in the art to account for these factors.

The composition may be administered about 1 to about 15 times per day, as needed, more preferably, about 2 to about 12 times per day, as needed, or most preferably, about 6 to about 10 times per day, as needed. The composition of the present invention may be administered in any acceptable dosage form, as described above, including, but not limited to, tablets, capsules, lozenges, troches, hard candies, powders, oral sprays, nasal sprays, gels, elixirs, syrups, chewable compositions, dental products, suspensions, and solutions.

Each dosage of the composition contains a safe and effective amount of the composition of the present invention. An effective amount for each therapeutic administration contains a total of about 0.1 gram to about 1 gram of the ingredients, which may be obtained from ginger and green tea. More preferably, an effective amount of the composition for each therapeutic administration contains a total of about 0.2 gram to about 0.5 gram of the ingredients which may be obtained from ginger and green tea. The amounts of the various ingredients of the composition administered in accordance with the method of the present invention are the same as given above for the composition of the present invention. Effective amounts for various forms of herpes can be determined by routine experimentation by a skilled person using common general knowledge and the examples of the invention contained herein.

Preferably, during each oral administration of the composition, the composition is held in the mouth for at least about 5 to about 60 minutes to enable the main ingredients of the composition to contact the mouth tissue or throat before it completely dissolves. More preferably, the composition is held in the mouth for at least about 15 to about 30 minutes.

When the composition is administered as a spray, the amounts each of the active ingredients may be reduced as the spray composition delivers the active ingredients more directly to the location where they are needed, as compared to a lozenge or capsule for example.

The following preferred ranges define compositions according to the invention that are suited for administration in a spray formulation according to the methods of the invention. Each gram of the composition administered in a spray according to the methods of the present invention preferably contains about 1 mg to about 10 mg of aquaresin® ginger. Most preferably, each gram of the composition contains about 3 mg to about 7 mg of aquaresin® ginger.

Each gram of the composition administered in a spray according to the methods of the present invention preferably contains about 1 mg to about 20 mg of green tea leaf extract. Most preferably, each gram of the composition contains about 4 mg to about 15 mg of green tea leaf extract.

Each gram of an optional embodiment of a composition administered in a spray according to the methods of present invention preferably contains about 1 mg to about 12 mg of soluble oleoresin turmeric. Most preferably, each gram of the composition contains about 4 mg to about 9 mg of soluble oleoresin turmeric.

The invention will be further illustrated by the examples given below which are not to be construed as limiting the invention in any way. The scope of the invention is to be determined by the claims appended hereto.

EXAMPLE 1

A composition of the Present Invention

A composition of the present invention formulated in the form of lozenges was prepared using the procedure described above. The ingredients of the lozenge are listed below:

| | |
|---|---|
| Sugar | 1 g |
| Slippery elm bark | 118 mg |
| Turmeric extract (5% curcumin) | 18 mg |
| Ginger root | 140 mg |
| Horseradish root | 70 mg |
| Green tea leaf extract (30% catechin and polyphenols) | 14 mg |

EXAMPLE 2

In Vitro Testing of Virucidal Activity of the Composition

The in vitro testing protocol for virucidal activity employed in this example uses human rhinovirus 16 (hereafter "HRV-16") as the target virus, and the MRC-5 cell line related to human tissues described by Jacobs et al., Characteristics of Human diploid MRC-5, Nature (London), 227:168–170 (1970) as the host cell for the HRV-16 viruses. Residual virus infectivity following incubation of the test substances with the virus was titrated on the MRC-5 cell line for rhinovirus growth by visually scoring the cytopathic effect (CPE) induced by virus replication through microscopic observation. More specifically, CPE was scored by observing ballooning/rounding cells in the MRC-5 culture.

To determine the virucidal activity, the composition of Example 1 (hereafter "Substance 1"), was employed at an initial dilution of 1/20 and then further diluted by serial dilutions in saline. The diluted compositions were incubated with HRV-16 for a set time period and then the reaction was terminated by adjustment to a neutral pH with cell infection media. The resultant solution was then titrated out on MRC-5 cells at a dilution of 1/10 across a testing plate to carry out the infection of the cells. Each plate housed a virus control, which contained only HRV-16 infected MRC-5 cells, and a cell control, which contained only uninfected MRC-cells.

The plates were further incubated for 4 days after the infection. Residual viral infectivity was measured using the assay discussed above. From the results shown in Tables 1–4, all of the controls on the plate worked well.

From the assay, it was concluded that Substance 1, at a 1/20 dilution, was effective in producing an HRV-16 viral log reduction of 1.50 ($-\log_{10}$ TCID$_{50}$) at the 1-minute incubation period. A 1/40 dilution of Substance 1 produced a log reduction of 1.00 ($-\log_{10}$ TCID$_{50}$) also at the 1-minute incubation period. After the 2-minute and 5-minute incubation periods, 1/2 log reductions in HRV-16 titer were achieved. Therefore, these results tend to indicate that a 1-minute contact time between Substance 1 and HRV-16 would produce the most effective viral titer reduction.

Table 1 shows the residual virus titers and log reductions of infectious Rhinovirus 16 on MRC-5 cells at one termination time point, of Substance 1 at different dilutions.

Tables 1–3 show the residual virus titers and log reductions of infectious HSV-1 on Vero cells at three different termination time points, of Substance 1 at different dilutions.

TABLE 1

| | 1 Minute Incubation | | |
|---|---|---|---|
| Dilutions of Substance 1 | HSV-1 Control Titer ($-\log_{10}$ TCID$_{50}$) | Residual HSV-1 titer ($-\log_{10}$ TCID$_{50}$) | HSV-1 log reductions ($-\log_{10}$ TCID$_{50}$) |
| 1/40 | 3.80 | 0.00 | 3.80 |
| 1/80 | 3.80 | 0.00 | 3.80 |
| 1/160 | 3.80 | 2.80 | 1.00 |
| 1/320 | 3.80 | 2.80 | 1.00 |
| 1/640 | 3.80 | 2.80 | 1.00 |

TABLE 2

| | 2 Minute Incubation | | |
|---|---|---|---|
| Dilutions of Substance 1 | HSV-1 Control Titer ($-\log_{10}$ TCID$_{50}$) | Residual HSV-1 titer ($-\log_{10}$ TCID$_{50}$) | HSV-1 log reductions ($-\log_{10}$ TCID$_{50}$) |
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

TABLE 3

| | 5 Minute Incubation | | |
|---|---|---|---|
| Dilutions of Substance 1 | HSV-1 Control Titer ($-\log_{10}$ TCID$_{50}$) | Residual HSV-1 titer ($-\log_{10}$ TCID$_{50}$) | HSV-1 log reductions ($-\log_{10}$ TCID$_{50}$) |
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

EXAMPLE 3

An Antimicrobial Lozengze of the Present Invention

An antimicrobial lozenge was made according to the formulation set forth below.

| | |
|---|---|
| 1) Dextrose | 865.0 mg |
| 2) Slippery Elm Bark | 150.0 mg |
| 3) Stearic Acid | 75.0 mg |

-continued

| | |
|---|---|
| 4) Ginger Root | 105.0 mg (Children) or 140.0 mg (Adult) |
| 5) Horseradish Root | 70.0 mg |
| 6) Honey Natural Flavor | 40.0 mg |
| 7) Turmeric Extract (5% Curcumin) | 15.0 mg |
| 8) Green Tea Leaf Extract (36% C&P) | 14.0 mg |
| 9) Silicon Dioxide | 14.0 mg |
| 10) Magnesium Stearate | 12.0 mg |
| 11) Sucralose/Splenda | 4.0 mg |
| Tablet Weight: | 1364.0 mg |

Note:
C&P as used herein means "catechols and phenols."

EXAMPLE 4

An Antimicrobial Spray of the Present Invention

An antimicrobial spray was made according to the formulation set forth below.

| | |
|---|---|
| (1) Slippery Elm Bark Extract | 18.52 mg |
| (2) Oleoresin Turmeric, Soluble (~8.5% Curcumin) | 8.82 mg |
| (3) Aquaresin ® Ginger | 7.0 mg |
| (4) Horseradish Flavor WONF | 0.62 mg |
| (5) Green Tea Leaf PE 50% Colorimetric | 14.0 mg |
| (6) Honey Natural Flavor | 40.0 mg |
| (7) Ethanol (95%) @ 5% | 68.2 mg |
| (8) Glycerine | 603.42 mg |
| (9) Distilled Water | 603.42 mg |
| Total Weight: | 1364.0 mg |

EXAMPLE 5

In Vitro Inhibitory Activity Against HSV-1

Procedure:
1. Five A549 24-well multiplates per virus strain were prepared.
2. Stock virus HSV-1 W was removed from the freezer. The virus was a clinical ocular isolate.
3. A stock formulation was prepared including the following ingredients:

TABLE 4

| Stock Formulation | |
|---|---|
| Component | Weight Percent, based on the total weight of the Composition |
| Turmeric Oleoresin | 0.6466 |
| Ginger Oleoresin | 0.6840 |
| Horseradish Oil | 0.06312 |
| Green Tea Powdered Extract | 0.4619 |
| Glycerin | 46.5723 |
| Ethanol | 5.0000 |
| Lipoid Lecithin | 0.5000 |
| Neobee ™ M-5 MCT oil | 5.0000 |
| Water | 41.0721 |
| Total | 100.0000 |

4. Different concentrations of the stock formulation were prepared, in water, by dilution. The final test composition concentrations that were tested were dilutions of the stock formulation to 80%, 20%, 1.0%, and 0.1% concentrations, in water.
5. 200 µl of the four different test compositions concentrations were aliquoted into screw cap 2 ml Sarstedt freezing tubes or sterile microfuge tubes. Into 2 additional tubes, 200 µl each of sterile water were aliquoted for injection and PBS. This resulted in a set of 6 tubes. The water control was used to determine whether water rather than physiologic PBS had any inhibitory activity on the viruses.
6. To each of the six tubes, 50 µl of stock virus were added and gently mixed.
7. The mixed compositions were incubated for 60 minutes at 37° C. in a water bath.
8. At the end of 60 minutes, serial 10-fold dilutions on the supernatants of the six tubes were performed and a standard titration of the samples was carried out. 50 µl was removed from the undiluted samples and added to 450 µl of OG for the −1 dilution. There was approximately 200 µl remaining to plate the undiluted samples.
9. 0 to −7 were plated for all the test composition samples of HSV-1. For the control samples (water and PBS), −2 to −7 were plated.

The results are given in Table 5 below.

TABLE 5

| | HSV-1 Results | | | | | | | | | |
|---|---|---|---|---|---|---|---|---|---|---|
| Serotype | Titer PBS Control ($Log_{10}$) | Titer 80% ($Log_{10}$) | LR 80% | Titer 20% ($Log_{10}$) | LR 1.0% | Titer 1% ($Log_{10}$) | LR 1.0% | Titer 0.1% ($Log_{10}$) | LR 0.1% | Titer Water Control ($Log_{10}$) | LR Water Control |
| HSV-1 W | 6.13 | 0.0 | −6.13 | 0.0 | −6.13 | 1.40 | −4.73 | 5.15 | −0.98 | 5.75 | −0.38 |

LR = Log Reduction in Titer compared to PBS Control;

Titer = pfu/ml

As can be seen from Table 5, the direct antiviral effect of the test compositions against an ocular isolate of HSV-1 was impressive. The test compositions achieved complete inhibition (6.13 log decrease in titer) at 80% and 20% concentrations, and a 4.73 log decrease in titer at a 1% concentration.

EXAMPLE 6

To Determine the in Vitro Antiviral Inhibitory Activity of Test Compositions Against Two Ocular Isolates of HSV-1, and Two Non-Ocular Isolates of HSV-2

Procedure:
1. Three A549 24-well multiplates were prepared per virus strain. (12 total plates.)
2. Stock viruses of HSV-1 W ($1.65 \times 10^7$ pfu/ml), HSV-1 Mckrae ($1.0 \times 10^7$ pfu/ml), HSV-2 ST186 ($5.4 \times 10^7$ pfu/ml), and HSV-2 12135 ($2.7 \times 10^5$ pfu/ml) were removed from the freezer. HSV-1 strains were clinical ocular isolates, while the HSV-2 strains were genital isolates.
3. The same test compositions were tested as in Example 5 above.
4. 200 µl of the four test composition concentrations were aliquoted into screw cap 2 ml Sarstedt freezing tubes or sterile microfuge tubes. Into 2 additional tubes, 200 µl each of sterile water were aliquoted for injection and PBS. Each virus strain had a set of six tubes. The water control was used to determine whether water, rather than physiologic PBS, had any inhibitory activity on the viruses.
5. To each of the six tubes, 50 µl of stock virus from a single virus strain were added and gently mixed.
6. The mixed compositions were incubated for 60 minutes at 37° C. in a water bath.
7. At the end of 60 minutes, serial 10-fold dilutions were performed on the supernatants of the six tubes and a standard titration of the samples was carried out. 50 µl was removed from the undiluted samples and added to 450 µl of OG for the −1 dilution. There were approximately 200 µl remaining to plate the undiluted samples.
8. 0 to −5 were plated for all the QR435 samples. For the control samples (water and PBS), −1 to −6 were plated.

Impressive direct antiviral activity of the test compositions against the ocular isolate of HSV-1 in Example 5, was confirmed in the current example. The results are given in Table 6. The test compositions demonstrated complete inhibition of infectious HSV-1 W at 80% (6.74 log decrease in titer), a 5.34 log decrease in titer at 20%, and a 5.14 log decrease in titer at 1%.

Impressive direct antiviral activity of the test compositions was also demonstrated against a second ocular isolate of HSV-1, (HSV-1 Mckrae). The test compositions demonstrated complete inhibition of infectious HSV-1 Mckrae at 80% (5.69 log decrease in titer), a 3.74 log decrease in titer at 20%, and a 4.09 log decrease in titer at 1%.

The test compositions also demonstrated potent direct antiviral activity against two clinical, genital isolates of HSV-2 (ST186 and 12135). The test compositions demonstrated complete inhibition of infectious HSV-2 STI 86 at 80% and 20% (6.43 log decrease in titer) and a 2.20 log decrease in titer at 1%. More impressively, the test compositions demonstrated complete inhibition of infectious HSV-2 12135 at 80%, 20%, and 1% (5.30 log decrease in titer) and a 4.60 log decrease in titer at 0.1%.

It is to be understood that even though numerous characteristics and advantages of the present invention have been set forth in the foregoing description, they are illustrative only. Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

What is claimed is:
1. A method for reducing the transmissivity of herpes, comprising the step of administering to a mammal that has been exposed to herpes or has contracted herpes, a safe and effective amount of composition comprising:
   a first ingredient selected from the group consisting of ginger extract, ginger powder, at least a part of a whole plant of ginger, a ginger tincture, and mixtures thereof;
   a second ingredient selected from the group consisting of green tea powder, green tea extract, at least a part of a whole plant of green tea, tinctures of green tea, and mixtures thereof;

TABLE 6

HSV-1 and HSV-2 Results

| Ad Serotype | Titer PBS Control ($Log_{10}$) | Titer 80% QR435 ($Log_{10}$) | LR 80% QR435 | Titer 20% QR435 ($Log_{10}$) | LR 20% QR435 | Titer 1% QR435 ($Log_{10}$) | LR 1.0% QR435 | Titer 0.1% QR435 ($Log_{10}$) | LR 0.1% QR435 | Titer Water Control ($Log_{10}$) | LR Water Control |
|---|---|---|---|---|---|---|---|---|---|---|---|
| HSV-1 W | 6.74 | 0.0 | −6.74 | 1.40 | −5.34 | 1.60 | −5.14 | 6.20 | −0.54 | 6.78 | +0.04 |
| HSV-1 Mckrae | 5.69 | 0.0 | −5.69 | 1.95 | −3.74 | 1.60 | −4.09 | 6.45 | +0.76 | 5.92 | +0.23 |
| HSV-2 ST186 | 6.43 | 0.0 | −6.43 | 0.0 | −6.43 | 4.23 | −2.20 | 6.02 | −0.41 | 6.51 | +0.08 |
| HSV-2 12135 | 5.30 | 0.0 | −5.30 | 0.0 | −5.30 | 0.0 | −5.30 | 0.70 | −4.60 | 5.30 | 0.0 |

LR = Log Reduction in Titer compared to PBS Control;
Titer = pfu/ml an acceptable carrier;

said amount being administered in a manner that results in direct contact of said composition with said herpes, such that said amount is effective, when administered, to reduce an incidence of transmissivity of herpes to another mammal exposed to said mammal, relative to an incidence of transmissivity of herpes from a mammal to which the composition has not been administered.

2. The method of claim 1, wherein the herpes virus is selected from the group consisting of HSV-1 and HSV-2.

3. The method of claim 1, wherein the herpes virus is selected from the group consisting of ocular herpes and genital herpes.

4. The method of claim 1, wherein the composition is administered in a form selected from the group consisting of a lozenge, a troche, a hard candy, a chewable composition, and a dental product.

5. The method of claim 1, wherein the composition is administered as a nasal spray or as a throat spray.

6. The method of claim 1, wherein the first ingredient is selected from a group consisting of ginger powder extract, ginger powder, and mixtures thereof; and the second ingredient is selected from the group consisting of green tea powder, green tea powder extract, and mixtures thereof.

7. The method of claim 1, wherein the first ingredient comprises ginger root powder and the second ingredient comprises green tea extract.

8. The method of claim 7, wherein each gram of the composition contains about 1 mg to about 20 mg of green tea extract, and about 1 mg to about 150 mg of ginger root powder.

9. The method of claim 1, wherein the composition further comprises a third ingredient selected from the group consisting of turmeric extract, one or more curcuminoid compounds selected from curcumin, desmethoxycurcumin, bis-desmethoxycurcumin, turmeric powder, parts of, or whole plants of turmeric, tinctures thereof, and mixtures thereof.

10. The method of claim 9, wherein the composition contains about 1 mg to about 20 mg of turmeric powder extract.

11. The method of claim 9, wherein the composition further comprises a fourth ingredient selected from the group consisting of horseradish root, horseradish flavor, horseradish oil, horseradish root extract, extracts from *Cochlearia Armoracia,* and mixtures thereof.

12. A method using a composition to reduce one or more of herpes virus, severity of symptoms of herpes, and incidence of symptoms of herpes, comprising the step of administering to a mammal that has been, or will be, exposed to herpes, an amount of a composition comprising:

a first ingredient selected from the group consisting of ginger extract, ginger powder, at least a part of a whole plant of ginger, a ginger tincture, and mixtures thereof;

a second ingredient selected from the group consisting of green tea powder, green tea extract, at least a part of a whole plant of green tea, tinctures of green tea, and mixtures thereof;

an acceptable carrier;

said amount being administered in a manner that results in direct contact of said composition with said herpes, such that said amount is effective, when administered, to reduce an incidence of contracting herpes by another mammal exposed to said mammal.

13. The method of claim 12, wherein the virus is selected from the group consisting of HSV-1 and HSV-2.

14. The method of claim 12, wherein the herpes virus is selected from the group consisting of ocular herpes and genital herpes.

15. The method of claim 12, wherein the composition is administered in a form selected from a group consisting of a lozenge, a troche, a hard candy, a chewable composition, and a dental product.

16. The method of claim 12, wherein the composition is administered as a nasal spray or as a throat spray.

17. The method of claim 12, wherein
the first ingredient is selected from a group consisting of ginger powder extract, ginger powder, and mixtures thereof; and
the second ingredient is selected from the group consisting of green tea powder, green tea powder extract, and mixtures thereof.

18. The method of claim 12, wherein the first ingredient comprises ginger root powder and the second ingredient comprises green tea extract.

19. The method of claim 18, wherein each gram of the composition contains about 1 mg to about 20 mg of green tea extract, and about 5 mg to about 150 mg of ginger root powder.

20. The method of claim 12, wherein the composition further comprises a third ingredient selected from the group consisting of turmeric extract, one or more curcuminoid compounds selected from curcumin, desmethoxycurcumin, bis-desmethoxycurcumin, turmeric powder, parts of, or whole plants of turmeric, tinctures thereof, and mixtures thereof.

21. The method of claim 20, wherein the composition contains about 1 mg to about 20 mg of turmeric powder extract.

22. The method of claim 20, wherein the composition further comprises a fourth ingredient selected from the group consisting of horseradish root, horseradish flavor, horseradish oil, horseradish root extract, extracts from *Cochlearia Armoracia,* and mixtures thereof.

23. A method for the prophylactic treatment of herpes, comprising the step of administering to a mammal that has been, or will be, exposed to herpes, an amount of a composition comprising:

a first ingredient selected from the group consisting of ginger extract, ginger powder, at least a part of a whole plant of ginger, a ginger tincture, and mixtures thereof;

a second ingredient selected from the group consisting of green tea powder, green tea extract, at least a part of a whole plant of green tea, tinctures of green tea, and mixtures thereof an acceptable carrier;

said amount being administered in a manner that will result in direct contact of said composition with said herpes, such that said amount is effective, when administered, to reduce an incidence of contracting herpes by said mammal.

24. The method of claim 23, wherein each gram of the composition contains about 1 mg to about 20 mg of green tea extract, and about 5 mg to about 150 mg of ginger root powder.

25. The method of claim 23, wherein the composition further comprises a third ingredient selected from the group consisting of turmeric extract, one or more curcuminoid compounds selected from curcumin, desmethoxycurcumin, bis-desmethoxycurcumin, turmeric powder, parts of, or whole plants of turmeric, tinctures thereof, and mixtures thereof.

26. The method of claim 25, wherein the composition contains about 1 mg to about 20 mg of turmeric powder extract.

27. The method of claim 25, wherein the composition further comprises a fourth ingredient selected from the group consisting of horseradish root, horseradish flavor, horseradish oil, horseradish root extract, extracts from *Cochlearia Armoracia*, and mixtures thereof.

28. The method of claim 3, where in the composition is formulated in a formulation selected from the group consisting of a capsule, a gel, an aqueous suspension, an ointment and a transmucosal drug delivery system.

29. The method of claim 14, where in the composition is formulated in a formulation selected from the group consisting of a capsule, a gel, an aqueous suspension, an ointment and a transmucosal drug delivery system.

30. The method of claim 23, where in the composition is formulated in a formulation selected from the group consisting of a capsule, a gel, an aqueous suspension, an ointment and a transmucosal drug delivery system.

31. The method of claim 1, wherein the first ingredient is ginger fluid extract; and the second ingredient is green tea fluid extract.

32. The method of claim 12, wherein the first ingredient is ginger fluid extract; and the second ingredient is green tea fluid extract.

33. The method of claim 23, wherein the first ingredient is ginger fluid extract; and the second ingredient is green tea fluid extract.

* * * * *